US009588063B2

(12) United States Patent
Jakkula et al.

(10) Patent No.: US 9,588,063 B2
(45) Date of Patent: Mar. 7, 2017

(54) SENSOR, MEASURING DEVICE, AND MEASURING METHOD

(71) Applicant: Senfit Oy, Oulu (FI)

(72) Inventors: Pekka Jakkula, Oulu (FI); Mikko Vuolteenaho, Kiiminki (FI); Markku Korhonen, Kajaani (FI); Vesa Fisk, Oulu (FI)

(73) Assignee: Senfit Oy, Oulu (FI)

( * ) Notice: Subject to any disclaimer, the term of this patent is extended or adjusted under 35 U.S.C. 154(b) by 147 days.

(21) Appl. No.: 14/725,566

(22) Filed: May 29, 2015

(65) Prior Publication Data
US 2015/0346126 A1 Dec. 3, 2015

(30) Foreign Application Priority Data

Jun. 2, 2014 (FI) ...................................... 20145503

(51) Int. Cl.
G01R 27/04 (2006.01)
G01R 27/32 (2006.01)
(Continued)

(52) U.S. Cl.
CPC ........... *G01N 22/04* (2013.01); *G01N 27/221* (2013.01); *G01R 27/06* (2013.01); *G01R 27/28* (2013.01); *G01N 27/223* (2013.01); *G01R 31/11* (2013.01)

(58) Field of Classification Search
CPC ........ G01N 22/00; G01N 27/62; G01N 27/64; G01R 27/06; G01R 27/28; G01R 31/11;
(Continued)

(56) References Cited

U.S. PATENT DOCUMENTS 5,864,239 A   1/1999  Adams et al.
6,798,216 B2  9/2004  Jannsen et al.
(Continued)

FOREIGN PATENT DOCUMENTS

CA   2065811 A1   10/1993
EP   0622344 A2   11/1994
(Continued)

OTHER PUBLICATIONS

European Search Report; Application No. EP 15170054, 2 pages, Oct. 9, 2015.
(Continued)

Primary Examiner — Jermele M Hollington
Assistant Examiner — Raul Rios Russo
(74) Attorney, Agent, or Firm — Hoffmann & Baron, LLP

(57) ABSTRACT

A sensor measures a sample in a measuring cell including a helix conductor. The shell structure of the measuring cell is made of an electrically non-conductive material. The measuring cell and at least part of the helix conductor are placeable inside a chamber. A radio-frequency signal input element couples a radio-frequency signal to the chamber to form a helix resonance. A radio-frequency signal output element is responsive to a helix resonance of the helix conductor and transmits a radio-frequency signal for measurement. A device for measuring a sample in a measuring cell includes the sensor, a radio-frequency signal source, and a measuring and control part. The radio-frequency signal source produces a radio-frequency signal to the input element. The measuring and control part measures a property of a sample on the basis of a resonance frequency.

11 Claims, 5 Drawing Sheets

(51) Int. Cl.
*G01N 22/04* (2006.01)
*G01R 27/06* (2006.01)
*G01R 27/28* (2006.01)
*G01N 27/22* (2006.01)
*G01R 31/11* (2006.01)

(58) Field of Classification Search
CPC ........ G01R 27/00; G01R 27/04; G01R 27/32; G01L 21/30; H01J 41/00; H01J 41/02
USPC ........... 324/76.11–76.83, 459, 600, 629, 637
See application file for complete search history.

(56) References Cited

U.S. PATENT DOCUMENTS

| | | | |
|---|---|---|---|
| 2007/0224692 A1* | 9/2007 | Agar | G01N 27/22 436/150 |
| 2009/0062637 A1* | 3/2009 | Hashimshony | G01R 27/2664 600/407 |
| 2009/0204346 A1* | 8/2009 | Xie | G01F 1/66 702/45 |

FOREIGN PATENT DOCUMENTS

| | | |
|---|---|---|
| GB | 2271637 A | 4/1994 |
| GB | 2 365 978 A | 2/2002 |
| JP | S6140546 A | 2/1986 |
| SU | 1262609 A1 | 10/1986 |
| WO | WO0216931 A1 | 2/2002 |
| WO | 2011/133046 A1 | 10/2011 |

OTHER PUBLICATIONS

Roussy et al., "Microwave Broadband Permittivity Measurement with a Multinnode Helical Resonator for Studying Catalysts", Measurement Science and Technology, vol. 12, No. 4, pp. 542-547 (Apr. 2001).

Meyer, W., "Helical Resonators for Measuring Dielectric Properties of Materials", IEEE Transactions on Microwave Theory and Techniques, vol. MTT-29, No. 3, pp. 240-247 (Mar. 1981).

Nyfors & Vainikainen, "Industrial Microwave Sensors", Artech House, pp. 116, 155, 191-192 (1989).

Official Action for corresponding Finnish Application No. 20145503, pp. 1-2, (Jan. 20, 2015).

* cited by examiner

SENSOR, MEASURING DEVICE, AND MEASURING METHOD

CROSS-REFERENCE TO RELATED APPLICATION

This application claims benefit to Finnish Application No. FI 20145503, filed Jun. 2, 2014, which is incorporated by reference herein in its entirety.

BACKGROUND

Field

The invention relates to a sensor, measuring device, and measuring method.

Description of the Related Art

A helix resonator has a helical conductor (helix) in an electrically conductive chamber. The radio-frequency resonance of the helix resonator depends, among other things, on the permittivity of the material inside the helical conductor. In the prior art, helix resonance has been used in hygrometry, for example.

However, in the chambers of measuring devices utilizing helix resonance, there are strong stray fields, which reduces the quality of the measuring field and degrades the measuring result. In other respects, too, there is a need to further develop resonance measurement utilizing a helical conductor.

SUMMARY

The object of the invention is to provide an improved solution. This is achieved by a sensor according to claim 1. The invention also relates to a device according to claim 10. The invention also relates to a method according to claim 13.

Preferred embodiments of the invention are disclosed in the dependent claims.

The device and method according to the invention provide several advantages. The stray field caused by the ends of the helix conductor can be reduced or it can be eliminated. An electric field can be made to penetrate a sample in an effective manner and the solution permits the use of a relatively low measuring frequency.

BRIEF DESCRIPTION OF THE DRAWINGS

The invention will now be described in more detail in connection with the preferred embodiments and with reference to the accompanying drawings, in which.

DETAILED DESCRIPTION

The following embodiments are presented by way of example. Even though the description may refer to "an" embodiment at different points, this does not necessarily mean that each such reference is to the same embodiment or that a feature only applies to one embodiment, but instead individual features of different embodiments may also be combined to produce other embodiments.

Figure 1:
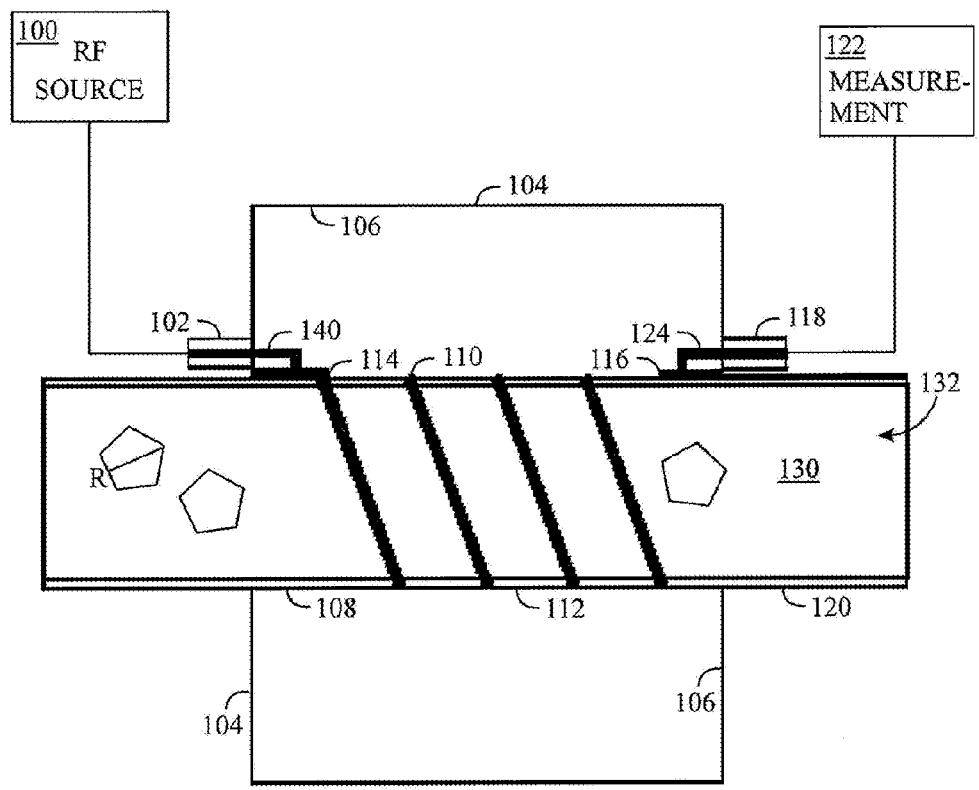
FIG. 1 shows an example of a sensor and measuring device.

Let us first examine an example of a measuring sensor and device by means of FIG. 1. A radio-frequency signal source 100 supplies a radio-frequency signal to an input element 102 that comprises a coaxial connector or microstrip structure or some other transmission conductor structure. In an embodiment, the radio-frequency source 100 may sweep over the frequency range being measured. In an embodiment, the measuring is based on self-oscillation, in which a radio-frequency signal entering and exiting the sensor is coupled to an amplifying element in such a manner that an oscillation circuit is created to oscillate at the frequency of the sensor resonance. The radio-frequency signal source 100 may comprise a voltage-controlled oscillator (VCO), direct digital synthesizer (DDS) or the like. From the input element 102, the radio-frequency signal moves on to a chamber 104, the shell structure 106 of which comprises electrically conductive material over its entire area. The electrically conductive material may be made of metal, such as aluminum or brass, for instance, without being limited to these, however. The shell structure 106 may be entirely electrically conductive, the inner surface of the shell structure 106 is electrically conductive, the outer surface of the shell structure 106 is electrically conductive, the interior of the shell structure 106 is electrically conductive, the outer surface of the shell structure 106 is electrically conductive, or a combination of the above. The purpose of the chamber 104 is to prevent the radio-frequency signal from leaking into the environment and radio-frequency interference from leaking into the chamber 104.

The input element 102 may comprise a projection 140 that conducts a radio-frequency signal and may extend into the chamber 104. The projection 140 may be approximately 10 mm long or shorter, for instance. The radio-frequency signal may be transmitted from the radio-frequency signal source 100 by a coaxial cable, for example, to the chamber 102, the projection 140 extending to which may be an inner conductor of said coaxial cable. The projection 140 may also be a microstrip or some other transmission means. The transmission of a radio-frequency signal from the radio-frequency signal source 100 to the input element 102 may also be done using other means than a coaxial cable, because the transmission method is not essential per se.

The device comprises a measuring cell 108 positioned or positionable inside the chamber 104. In an embodiment, the measuring cell 108 may be an open or closable measuring vessel that is filled with the sample 130 to be measured for measuring. The measuring vessel can be emptied for the next measurement. In an embodiment, the measuring cell 108 may be a tubular structure with an inside cavity, which is a space 132 at least partly enclosed by the measuring cell 108. The cross-section of the cavity may be angular like a square or a polygon, or the cross-section may be round like a circle or ellipse. The measuring cell 108 may be part of a tubular structure 120 that continues outside the chamber 104, and the measuring cell 108 is the part of the tubular structure 120 that is inside the chamber 104. In the cavity of the tubular measuring cell 108, the sample 130 being measured can flow as a continuous or discrete flow. The wall structure 112 of the measuring cell 108 is made of electrically non-conductive material. The electrically non-conductive material may be plastic, ceramics, or glass, for instance.

The device also comprises a helix conductor 110 that is located at the measuring cell 108. Typically, the helix conductor 110 is outside the space 132 enclosed by the measuring cell 108, even though in an embodiment, the helix conductor 110 may be on the inner surface of the measuring cell 108. Because the helix conductor 110 is not in the space 132 enclosed by the measuring cell 108, the helix conductor 110 also does not prevent the flow of the sample 130 in the measuring cell 108 or impede the filling of the measuring cell 108 with the sample 130. As the name implies, the helix conductor 110 is made of electrically conductive material that may be metal, such as aluminum, copper, silver, or gold. The helix conductor 110 serves as the base for the helix resonator. The helix conductor 110 is a coil that forms a thread, i.e. helix. There may be one or more laps in the thread. The more laps there are, the lower the lowest resonance frequency is. The helix conductor 110 creates inside the thread of the helix conductor 110 an electric field in the longitudinal direction of the helix conductor 110, which efficiently penetrates inside the measuring cell 108 and sample 130 in the electric field of the helix conductor 110.

In the embodiment of FIG. 1, the helix conductor 110 is closed at both ends 114, 116 in relation to the electrically conductive shell structure 106. In such a case, the helix conductor 110 is galvanically coupled to the shell structure 106 of the chamber 104. The projection 140 of the input element 102 is thus coupled to the end 114 short-circuited to the chamber 104 of the helix conductor 110. Correspondingly, the projection 124 of the input element 118 is coupled to the end 116 short-circuited to the chamber 104 of the helix conductor 110. This way, in the short-circuited and grounded ends 114, 116 of the helix conductor 110, the radio-frequency current is at its maximum and the voltage is at its minimum, and the strength of the electric field is zero, in which case no interfering stray field is formed at the ends 114, 116 of the helix conductor. This improves measuring accuracy.

In an embodiment, the helix conductor 110 may comprise a metal band wound around the measuring cell. The band-like structure may be embedded in the wall structure 112 of the measuring cell 108.

In an embodiment, the helix conductor 110 may comprise a conductor coated around the measuring cell 108. The coating can be done by electrolysis, vaporization or sputtering, for example.

In an embodiment, several resonances are formed on the helix conductor 110, in which the length of the helix conductor 110 is half a wavelength λ/2 at the lowest resonance frequency and an entire wavelength λ at the next resonance. In general, the following applies to resonance wavelengths and the length P of the helix conductor 110: $P=N*(\lambda/2)$, where N is an integer 1, 2, 3, . . . . In an embodiment, the width of the helix conductor 110 may be approximately 1 mm to 1 cm, for instance.

The measuring cell 108 and helix conductor 110 are placeable inside the chamber 104. Both ends 114, 116 of the helix conductor 110x are coupled to the shell structure 106 of the chamber 104 in the same manner. In the example of FIG. 1, the helix conductor 110 is coupled at both ends 114, 116 galvanically to the shell structure 106.

When a radio-frequency signal is coupled to the helix conductor 110, a radio-frequency current is formed therein to resonate at one or more helix resonances caused by the helix conductor 110. The frequency of said one or more helix resonances depends on the sample 130 in the measuring cell 108 within the sphere of influence of the helix conductor 100.

The radio-frequency current resonating in the helix conductor 110 is detected by a radio-frequency signal output element 118 that transmits a signal corresponding to the radio-frequency resonance to a measuring and control part 122. The measuring device measures the sample in the measuring cell 108 with the frequency of the resonating radio-frequency current formed in the helix conductor 110. The wavelength corresponding to the resonating frequency may be greater than the largest interior measurement of the chamber 104. The radiation scattering caused by a grainy sample 130 is prevented and a good penetration into the sample 130 is achieved with this type of low frequency.

The output element 118 may comprise a projection 124 conducting a radio-frequency signal, which may extend into the chamber 104. The length of the projection 124 may be approximately 10 mm or shorter, which makes for an efficient coupling of the radio-frequency resonance signal to the output element 118. The radio-frequency resonance signal can be transmitted from the resonating helix conductor 110 to the measuring and control part 122 with a coaxial cable, for instance, the inner conductor of which may be the projection 124 extending into the chamber 104. The projection 124 may also be a microstrip or some other corresponding structure. In addition, the transmission of the radio-frequency signal from the output element 118 to the measuring and control part 122 can also be done using other means than the coaxial cable, because the transmission method is not essential per se.

The measuring and control part 122 measures one or more properties of a sample 130 in the measuring cell 108 on the basis of the resonance frequency, resonance Q value and/or signal level of the radio-frequency signal. On the basis of one or more resonance frequencies, it is possible to determine the amount of water, water content, moisture or the like in the sample 130. A water-related property can be measured, because the relative permittivity $\epsilon_r$ of water is usually higher ($\epsilon_r$=81) than the relative permittivity (below 10) of electrically non-conductive, solid materials, for instance. Thus, the resonance frequency only changes in accordance with the relative proportion of water in the sample 130. This way, it is also possible to determine the dry content. The field of application may be biomaterial hygrometry or dry content measurement of sewage sludge, without being restricted to these, however. The measurements can also determine the amount of gas in liquid, amount of water in gas, amount of water in oil, amount of oil in water, amount of oil in alcohol, and amount of alcohol in oil. In general, a measurement may determine the mixing ratio of two or more agents and/or the amounts of two or more agents.

Figure 7:
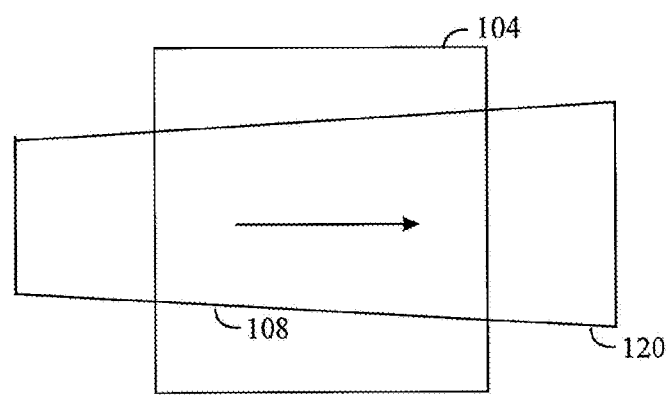
FIG. 7 shows an example of a conical measuring cell.

The measuring and control part 122 may comprise at least one processor 700 and at least one memory 702 that contains a computer program code (see FIG. 7). Said at least one memory 700 together with said at least one processor 702 and computer program code may implement the measuring and control operations to be performed in the measuring device. The measuring and control part 122 may control the radio-frequency signal source 100 to produce a radio-frequency signal to the input element 102. The measuring and control part 122 may then measure at least one property of a sample 130 on the basis of at least one resonance frequency.

In the embodiment of FIG. 1, the projection 140 of the input element 102 supplying the radio-frequency signal is galvanically coupled to the first end 114 of the helix conductor 110. The first end 114 of the helix conductor 110 is, in turn, galvanically coupled to the shell structure 106. This way, the projection 140 is short-circuited through the helix conductor 110 to the shell structure 106 in such a manner that a transmission loop is formed to couple the radio-frequency signal inductively to the helix conductor 110. The current circulating in the loop is, thus, transmitted to the ground through the helix conductor 110. The earth conductor of the transmission line supplying the radio-frequency signal of the input element 102 is then coupled to the shell structure 106 of the chamber 104.

Typically, the transmission line outer conductor that encloses the center conductor transmitting the radio-frequency signal is coupled to the shell structure 106 of the chamber 104. The center conductor of the transmission line is galvanically coupled to the projection 140 of the input element 102. In an embodiment, the length of the projection 140 in a loop coupling may be approximately 10 mm or shorter. This refers to the length of the projection 140 inside the chamber 104 from the input element 102 to the helix conductor 110 that is coupled to the shell structure 106 of the chamber. In the loop coupling, the length of the projection 140 may be approximately 5 mm in the horizontal direction and approximately 2 mm in the vertical direction, for example. However, the size of the loop is not restricted to these dimensions.

In the embodiment of FIG. 1, the projection 124 of the output element 118 is also galvanically coupled to the second end 116 of the helix conductor 110. The second end 116 of the helix conductor 110 is, in turn, galvanically coupled to the shell structure 106. This way, the projection 124 is short-circuited through the helix conductor 110 to the shell structure 106 in such a manner that a transmission loop is formed to couple the radio-frequency signal inductively from the resonating helix conductor 110 to the output element 118. The current circulating in the loop is, thus, transmitted to the ground through the helix conductor 110. The earth conductor of the transmission line receiving the radio-frequency signal of the output element 118 is coupled to the shell structure 106 of the chamber 104. The transmission line outer conductor that encloses the center conductor transmitting the radio-frequency signal is typically coupled to the shell structure 106 of the chamber 104. The center conductor of the transmission line is, in turn, galvanically coupled to the projection 124 of the output element 118. In an embodiment, the length of the projection 124 in the loop coupling may be approximately 10 mm or shorter. This refers to the length of the projection 124 inside the chamber 104 from the input element 102 to the helix conductor 110 that is coupled to the shell structure 106 of the chamber. In the loop coupling, the length of the projection 124 may be approximately 5 mm in the horizontal direction and approximately 2 mm in the vertical direction, for example. However, the size of the loop is not restricted to these dimensions.

Figure 2:
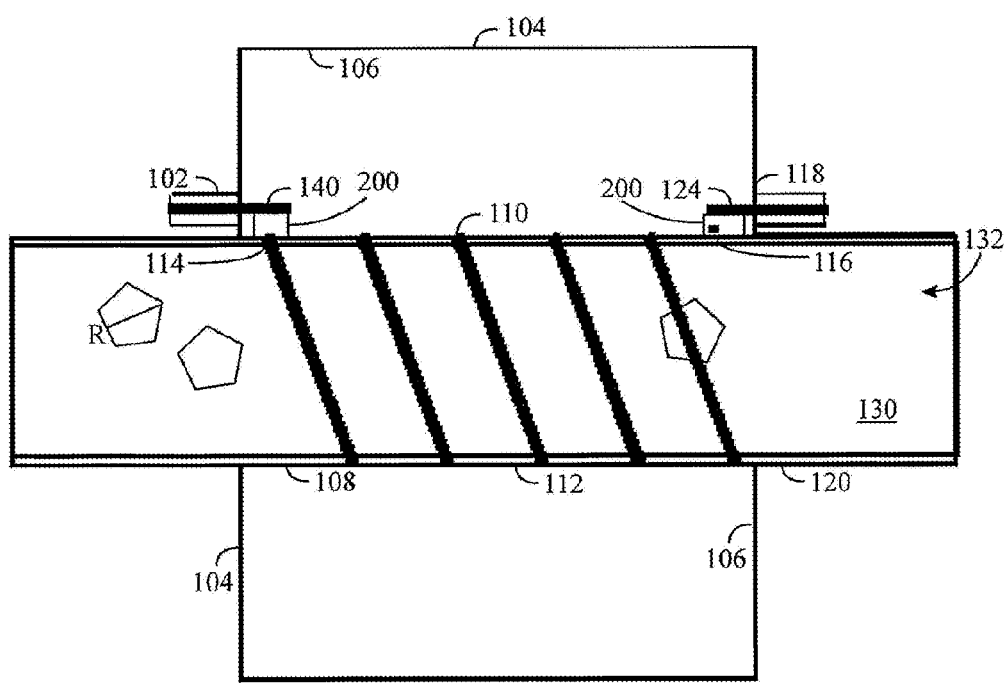
FIG. 2 shows a second example of a sensor.

FIG. 2 illustrates capacitive coupling. In this embodiment, the helix conductor 110 is at both ends 114, 116 open in relation to the electrically conductive shell structure 106. Further, in this embodiment, the projection 140 of the input element 102 is not galvanically coupled to the helix conductor 110 or to the shell structure 106 of the chamber.

However, the earth conductor of the transmission line supplying the radio-frequency signal of the input element 102 is coupled to the shell 106 of the chamber 104. The projection 140 of the input element 102 is close to the end 114 of the helix conductor 110, which is why the coupling of the radio-frequency signal from the projection 140 to the end 114 of the helix conductor 110 is capacitive. This type of coupling also centers the stray field of the helix conductor 110 end 114, 116 to the projection 140, 124, in which case the stray field does not affect the material measurement so much.

Chamber coupling is to the entire helix conductor 110, if the projection 140 is at a distance from the helix conductor 110. The terms chamber coupling and capacitive coupling are apparent to a person skilled in the art and define the coupling method clearly without needing to determine the distance between the projection 140 and the helix conductor 110 end 114. In addition, the coupling area or point (the end 114 of the helix conductor or the entire helix conductor/center part of the helix conductor) in the helix conductor 110 clarifies the difference in the coupling method. Capacitive coupling directly to the end of the helix conductor 110 is stronger than chamber coupling, which takes place through a stray field in the chamber 104, and, therefore, effectively produces a better-quality measuring signal. In an embodiment, the distance between the projection 140 and helix conductor 110 end 114 is shorter than approximately 10 mm. In an embodiment, the distance between the projection 140 and helix conductor 110 end 114 is approximately 5 mm or less. In an embodiment, the distance between the projection 140 and helix conductor 110 end 114 is approximately 3 mm or less.

In an embodiment, which is more common than that of FIG. 1 and which is shown in FIGS. 1 and 2, the input element 102 of the radio-frequency signal may couple a radio-frequency signal directly to one end 114 of the helix conductor 110. The output element 118 of the radio-frequency signal is directly coupled to a radio-frequency electric field at the other end 116 of the helix resonator 110. Direct coupling refers to the coupling of a supplied radio-frequency signal directly to the end 114 of the helix conductor 110. In the inductive coupling of FIG. 1, the projection 140 of the input element 102 is galvanically coupled through a loop coupling to the helix conductor 110 end 114, which is, in turn, coupled to the grounded shell structure 106 of the chamber 104. In the capacitive coupling of FIG. 2, the direct coupling is based on the fact that the projection 140 of the input element 102 is close to the end 114 of the helix conductor 110 in the manner defined by the capacitive coupling. The direct coupling of the electric field in the chamber 104 to the output element 118 can be understood in the corresponding manner.

In an embodiment according to FIG. 2, the projection 140 of the input element 102 may be fastened to a coupling piece 200 that is made of electrically non-conductive material. The coupling piece 200 is on one side thereof fastened to the end 114 of the helix conductor 110 and thus the coupling piece 200 maintains a controlled and at least nearly unchanged distance between the projection 140 and helix conductor 110 end 114 even under different temperatures and vibration, which improves level measurement accuracy. The coupling piece 200 may be made of plastic, ceramics or glass, for example. The coupling piece 200 may be fastened by glue, for instance. The fastening of the coupling piece 200 may also extend to the outer surface of the measuring chamber 108. The projection 124 of the output element 118 may, in the same manner as the projection 140 of the input element 102, be fastened to the coupling piece 200 that is made of electrically non-conductive material.

Figure 3:
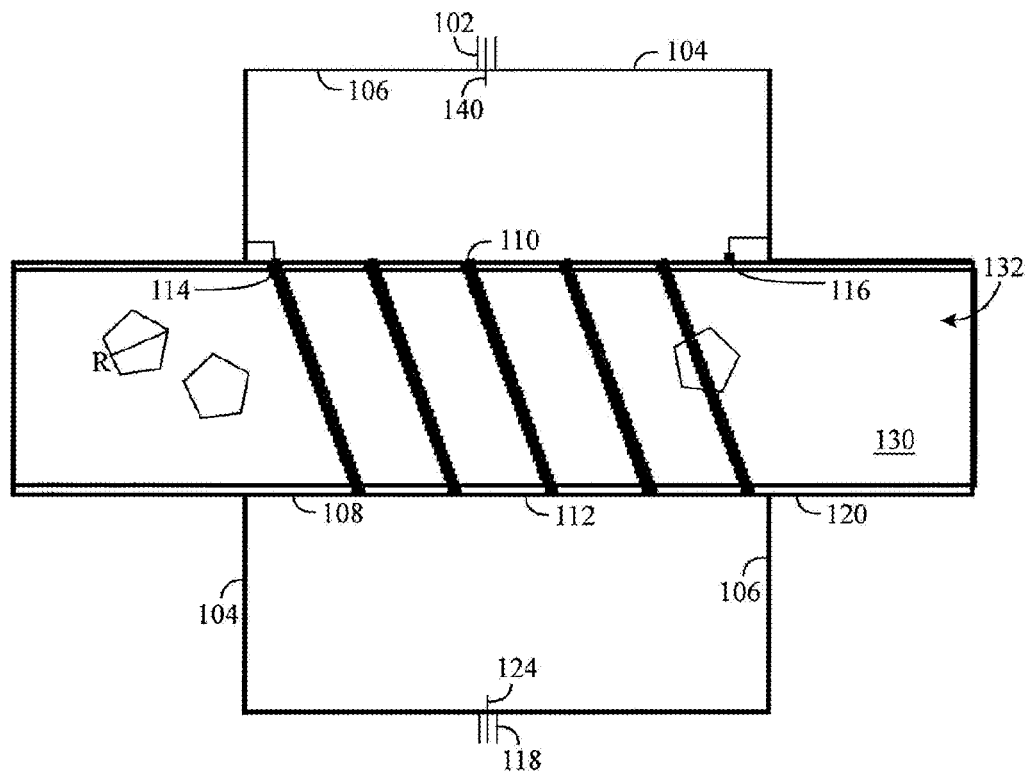
FIG. 3 shows a third example of a sensor.

In an embodiment, shown in FIG. 3, the device comprises a radio-frequency signal input element 102 that is positioned at the shell structure 106 of the chamber 104, perpendicular to the longitudinal axis of the helix conductor 110, in the area between the ends 114 and 116 of the helix structure 110 to couple the radio-frequency signal by chamber coupling through a stray field in the chamber 104 to the helix resonator 110. As already stated earlier, chamber coupling differs from capacitive coupling. In the embodiment of FIG. 3, the helix conductor 110 is at both ends 114, 116 closed in relation to the electrically conductive shell structure 106. In such a case, the helix conductor 110 is galvanically coupled to the shell structure 106 of the chamber 104.

In the embodiment of FIG. 3, the radio-frequency signal output element 118 may be positioned at the shell structure 106 of the chamber 104, perpendicular to the longitudinal axis of the helix conductor 110, on a different side in view of the input element 102, and the output element 118 receives a radio-frequency electric field through chamber coupling from the chamber 104. In an embodiment, the input element 102 and output element 118 may also be side by side on the same side of the chamber 104.

In an embodiment, the device measures a sample 130 in the measuring cell 108 on a wavelength that is greater than the granular size R of the sample 130 in the measuring cell 108. The granular size may refer to the diameter of the granule.

Figure 4:
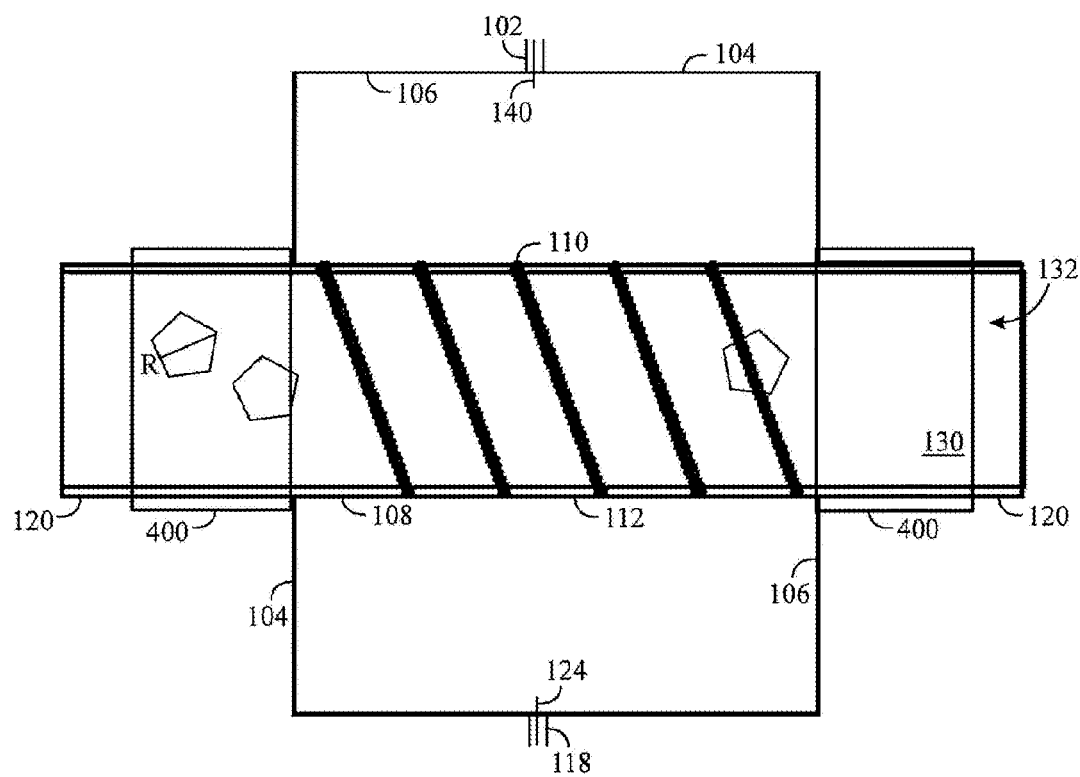
FIG. 4 shows an example of protective structures that reduce interference between the environment and the measuring chamber.

FIG. 4 shows an embodiment, in which at the tubular structure 120 passing through the chamber 104 and extending from the chamber 104, there are, outside the measuring chamber 108, protective shells 400 made of electrically conductive material. The protective shells 400 may be tubular parts around the tubular structure 120 on the outer surface, inside the structure 120 or on the inner surface of the structure 120. The cut-off frequency of the protective shells 400 is higher than the highest frequency generated in the chamber 104, which means that radio-frequency electromagnetic radiation cannot leak out of the chamber 104 nor can interfering radio-frequency electromagnetic radiation from the environment enter the resonator. The protective shells 400 improve the Q (Quality) value of the resonance and make measuring immune to external electromagnetic interference.

Figure 5:
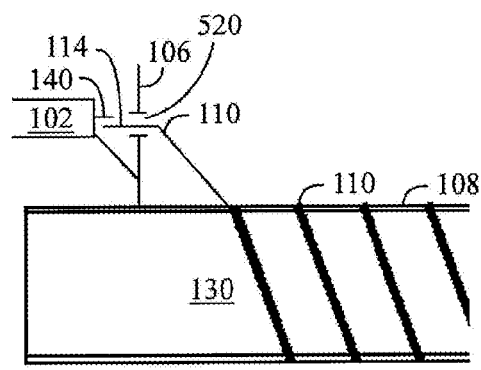
FIG. 5 shows an example of a capacitive coupling outside the chamber.

FIG. 5 shows a capacitive coupling between the input element 102 and helix conductor 110, which is, in principle, similar to the coupling of FIG. 2. In this embodiment, too, the end 114 of the helix conductor 110 may extend outside the chamber 104 through an opening 520 in the chamber 104. The output element 118 and the projection 124 connected thereto can also be coupled in the same manner as the input element 102 and projection 140 of FIGS. 5 and 6.

Figure 6:
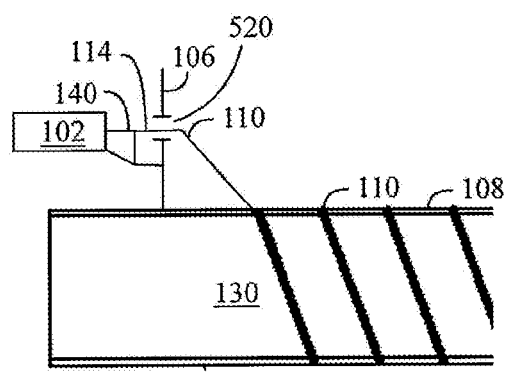
FIG. 6 shows an example of an inductive coupling outside the chamber.

FIG. 6 shows the inductive coupling between the input element 102 and helix conductor 110, which is, in principle, similar to the coupling of FIG. 1. In the embodiment of FIG. 6, the end 114 of the helix conductor 110 may extend outside the chamber 104 through the opening 520 in the chamber 104.

FIG. 7 shows an embodiment, in which a cavity 500 inside the tubular structure 120 expands in the flow direction of the sample, which is indicated by an arrow in FIG. 7. This way, the measuring chamber 108 and tubular structure 120 will not block at all because of the sample or as easily as a uniform tubular structure 120.

Figure 8:
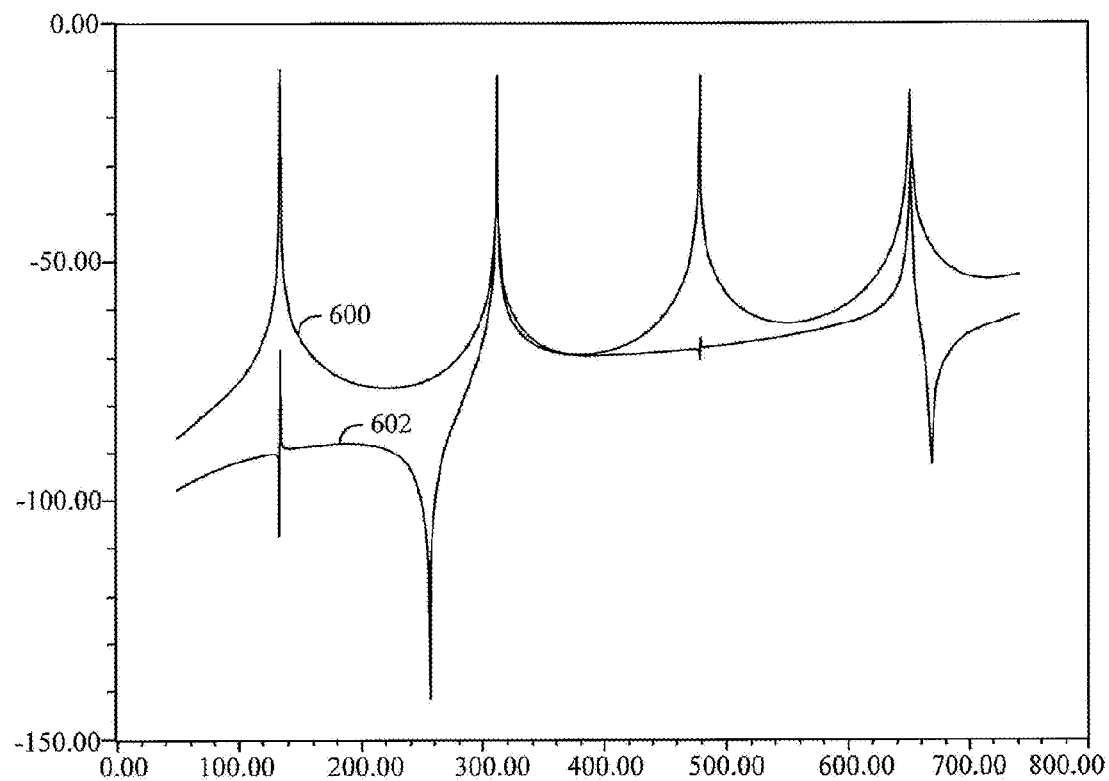
FIG. 8 shows an example of simulation curves.

FIG. 8 shows an example of a simulation performed by the solution described in this patent application, curve 600, and a measurement made in the conventional way, curve 602. In this measurement, the measuring cell 108 was 75 mm in diameter and the helical conductor 110 had three laps around the measuring cell 108. The vertical axis shows the attenuation of the radio-frequency signal in the resonator in decibels and the horizontal axis shows the frequency from 0 to 800 MHz. As the curves 600, 602 show, all four resonances of the solution described in the patent application are very clear and of the same shape. The resonance peaks are at least almost at the same height and the half-band width of the resonance peaks is narrow. In the prior art, i.e. conventional, measurement, the first resonance is not detectable at all and there is strong attenuation before the second resonance. The third resonance is the weakest to detect by the prior art, which is because the resonance frequency does not couple properly. The fourth resonance is split asymmetric in the middle, in which case an accurate definition of the Q value is not possible. The simulator results were also verifiable by measurements.

The above measurement can be implemented in a process pipe in such a manner that no flow barrier goes into the pipe, that is, the sensor is only formed of a straight, smooth pipe part. The measurement also works well with non-homogenous materials without the location of the material piece in the cross-sectional area of the measuring cell 108 affecting the measuring result.

The measuring device can be coupled to measure materials flowing inside plastic pipes and tubes by making the sensor a clamp-on version that may be installed without cutting the tube. The helix conductor that is open at both ends is wound around the pipe and the rest of the equipment may be assembled in parts around the pipe without cutting the pipe. Another possible embodiment is to push a separate plastic pipe inside the measuring cell 108, which means that the measuring cell is not subjected to process pressures.

The response of a sensor with a helix conductor may contain a large number of resonance frequencies, which makes the compensation of the effect of material conductivity possible by using at least two resonances with differing frequencies. This way, the measuring and control part 122 may determine the conductivity of the material being measured on the basis of the levels and/or Q factors of at least two resonances having different frequencies. The measuring and control part 122 may use said conductivity in determining at least one property of the sample 130.

Usually, the frequencies need to differ substantially from each other, i.e. more than the frequency resolution of the measuring device. The intensities of the resonances depend on the conductivity of the electrically conductive material as a function of the resonance frequency. The greater the difference in strength between two resonances having a different frequency, the greater the conductivity of the sample 130. For instance, in the simulation of FIG. 6, the conductivity of the sample 130 was small.

A two-parameter measurement permits the measurement of two properties (e.g. moisture and density) of a material. It is then possible to measure at least two of the following: resonance frequency, the level of said at least one resonance frequency, and the Q value of the resonance frequency.

In two-parameter measurement, it is possible to use not only the resonance frequency of the resonator, but also, as a second parameter, the level and/or Q value of the signal for the purpose of obtaining a density compensation algorithm for hygrometry.

The responses of the created resonances in the flow direction of the measuring cell may be one-peaked or multi-peaked. If a two-peaked resonance is selected, the measurement of the flow rate is made possible through auto-correlation. If the inner cross-sectional area of the measuring cell 108 is known, which is normal, it is also possible to measure the material quantity flow with auto-correlation.

If a resonance is used, the response of which is sensitive in the longitudinal direction in the center of the helix conductor 110 and non-sensitive at the ends of the helix conductor, the solution is as unambiguous as possible, and the leakage from the sensor is minimal. In the case of open ends, the electric field is at its greatest at the ends 114, 116 of the helix conductor 110 close to the outlet pipe, in which case external interference may, in spite of chopping frequency pipes 400, be greater than in the short-circuited model. In addition, the open ends 114, 116 of the helix conductor 110 may affect the resonance frequency formed by means of the helix conductor 110.

Figure 9:
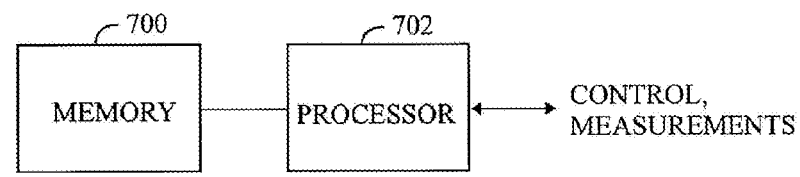
FIG. 9 shows an example of a measuring and control part.

FIG. 9 shows a measuring and control part 122 that comprises one or more memories 700 and one or more processors 702. In addition, the measuring and control part 122 comprises one or more suitable computer programs for performing the measurements and controlling the measuring device.

Figure 10A:
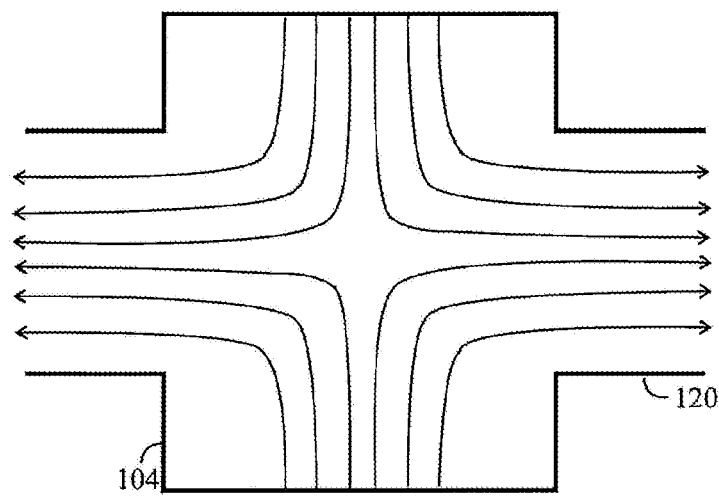
FIG. 10A shows an example of field lines of an electric field in a measuring cell with a coupling according to FIG. 1 at the lowest resonance.
Figure 10B:
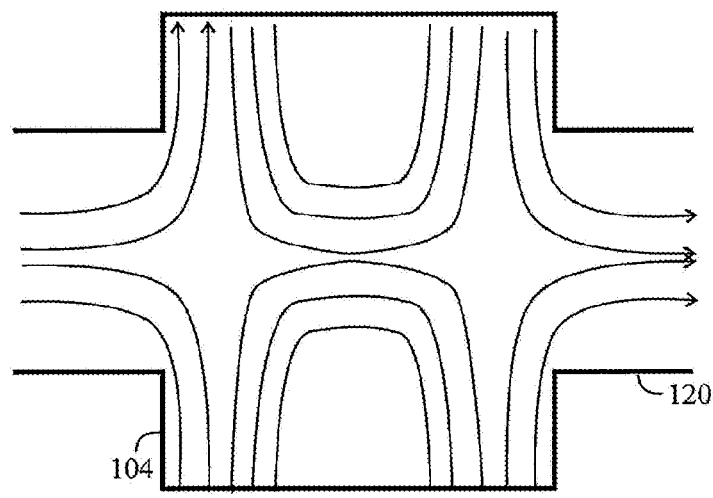
FIG. 10B shows an example of field lines of an electric field in a measuring cell with a coupling according to FIG. 1 at the second lowest resonance.

Electric field patterns of the two lowest resonances are shown in FIGS. 10A and 10B. The electric field of FIG. 10A corresponds to the lowest resonance in the coupling of FIG. 1. The electric field of FIG. 10B corresponds to the second lowest resonance in the coupling of FIG. 1. The electric field is parallel to the longitudinal axis of the tubular measuring cell in both cases. On the basis of FIGS. 10A and 10B, it is easy to see that supplying a resonator with a prior-art chamber coupling to the chamber 104 is not easily done even with these two waveforms, because the direction of the electric field in them is clearly different and partly at a 90-degree angle. This explains the weak couplings at some resonances shown in FIG. 8. At higher resonances the waveforms are even more complex. When supplying directly to the helix conductor 110, this problem does not exist, because the end 114 of the helix conductor 110 is always either short-circuited or open.

Figure 11:
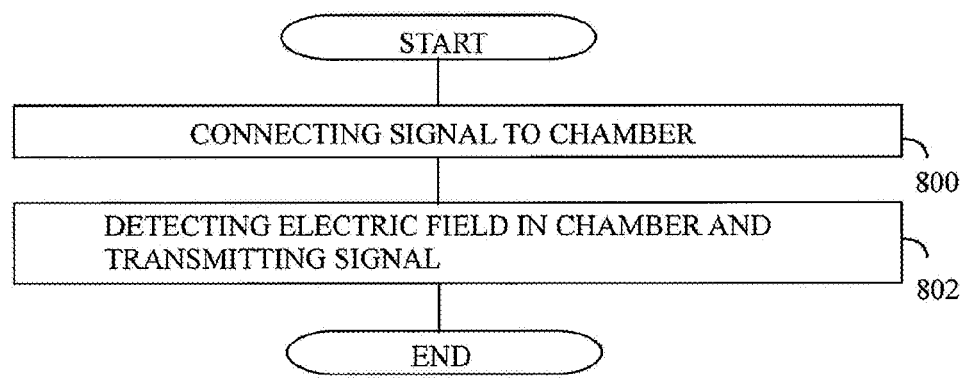
FIG. 11 shows an example of a flowchart of the method.

FIG. 11 shows an example of the method. In step 800, a radio-frequency signal with a wavelength greater than the largest interior measurement of the chamber 104 is coupled with the radio-frequency signal input element 102 to the chamber 104, which comprises a shell structure 106 made of electrically conductive material, to form a helix resonance in the chamber 104 by means of the helix conductor 110 of the measuring cell 108 in the chamber 104, both ends 114, 116 of the helix conductor 110 having the same coupling to the shell structure 106 of the chamber 104, while the shell structure 112 of the measuring cell 108 is made of an electrically non-conductive material. In step 802, a radio-frequency electric field formed in the chamber 104 is detected with the output element 124 of the radio-frequency signal, and the radio-frequency signal is transmitted for measuring.

When the measuring device comprises at least one processor 702, at least one memory 700 with a computer program stored therein, the computer program and memory 700 are able, together with said at least one processor 702, to make the measuring device perform at least some of the necessary operations in the measuring device.

The computer program may be placed on a computer program distribution means for the distribution thereof. The computer program distribution means is readable with a data processing device, and it may encode computer program commands for controlling the operation of the measuring device.

The distribution means, in turn, may be a solution known per se for distributing a computer program, for instance a computer-readable medium, a program storage medium, a computer-readable memory, a computer-readable software distribution package, a computer-readable signal, a computer-readable telecommunication signal or a computer-readable compressed software package.

Even though the invention has been described above with reference to the examples according to the accompanying drawings, it is clear that the invention is not restricted thereto but may be modified in many ways within the scope of the accompanying claims.

What is claimed is:

1. A sensor for measuring a sample in a measuring cell, the sensor comprising:
    a helix conductor that is at both ends short-circuited to a shell structure and located at the measuring cell elsewhere than in the space enclosed by the measuring cell, the shell structure of the measuring cell being made of an electrically non-conductive material;
    a chamber, inside which the measuring cell and at least part of the helix conductor are placeable and which comprises a shell structure made of an electrically conductive material, the coupling of both ends of the helix conductor to the shell structure of the chamber being the same;
    a radio-frequency signal input element that is adapted to couple with loop coupling a radio-frequency signal inductively to the helix conductor in the chamber for the purpose of creating at least one helix resonance in the helix conductor; and
    a radio-frequency signal output element that is responsive to at least one helix resonance of the helix conductor by forming with loop coupling an inductive coupling to the resonating helix conductor and that is adapted to transmit a radio-frequency signal for measurement.

2. The sensor of claim 1, wherein the sensor comprises a radio-frequency signal input element adapted to couple a radio-frequency signal with direct coupling to one end of the helix conductor; and a radio-frequency signal output element adapted to receive a radio-frequency signal with direct coupling from the other end of the helix resonator.

3. The sensor of claim 1, wherein the sensor is adapted to operate on a wavelength that is greater than the largest granular size of the sample in the measuring chamber.

4. The sensor of claim 1, wherein the sensor comprises a radio-frequency signal input element that is located at the shell structure of the chamber perpendicular to the longitudinal axis of the helix conductor in the area between the ends of the helix conductor and that is adapted to couple with chamber coupling a radio-frequency signal to the chamber for the purpose of forming a helix resonance; and a radio-frequency signal output element that is located at the shell structure of the chamber in the area between the ends of the helix conductor on a different or same side in view of the input element and that is adapted to receive a radio-frequency signal with chamber coupling.

5. The sensor of claim 1, wherein the sensor comprises electrically conductive protective structures in a tubular structure extending out of the chamber and comprising a measuring cell.

6. The sensor of claim 1, wherein the sensor comprises in the flow direction of the sample a tubular structure with an expanding cavity, and a measuring cell.

7. A device for measuring a sample in a measuring cell, wherein the device comprises a sensor for measuring a sample in a measuring cell, the sensor comprising:
- a helix conductor that is at both ends short-circuited to a shell structure and located at the measuring cell elsewhere than in the space enclosed by the measuring cell, the shell structure of the measuring cell being made of an electrically non-conductive material;
- a chamber, inside which the measuring cell and at least part of the helix conductor are placeable and which comprises a shell structure made of an electrically conductive material, the coupling of both ends of the helix conductor to the shell structure of the chamber being the same;
- a radio-frequency signal input element that is adapted to couple with loop coupling a radio-frequency signal inductively to the helix conductor in the chamber for the purpose of creating at least one helix resonance in the helix conductor; and
- a radio-frequency signal output element that is responsive to at least one helix resonance of the helix conductor by forming with loop coupling an inductive coupling to the resonating helix conductor and that is adapted to transmit a radio-frequency signal for measurement;
- a radio-frequency signal source; and
- a measuring and control part, the radio-frequency signal source being adapted to produce a radio-frequency signal to the input element, the measuring and control part being adapted to measure at least one property of the sample on the basis of at least one resonance frequency.

8. The device of claim 7, wherein the measuring and control part is adapted to determine the values of at least two parameters related to the resonance and to form at least two properties of the sample on the basis of the determined parameter values.

9. The device of claim 7, wherein the measuring and control part is adapted to determine the conductivity of the measured material on the basis of the levels or quality factors of at least two resonances having different frequencies, and the measuring and control part is adapted to use said conductivity to determine at least one property of the sample.

10. The device of claim 7, wherein the measuring and control part comprises at least one processor; and at least one memory that contains a computer program code, said at least one memory together with said at least one processor and computer program code being adapted to cause the measuring device to:
- couple through the input element to the chamber, which comprises a shell structure made of electrically conductive material, a radio-frequency signal, which has a wavelength greater than the largest interior measurement of the chamber, for the purpose of forming a helix resonance by means of the helix conductor of the measuring cell in the chamber, both ends of the helix conductor having the same coupling to the shell structure of the chamber, while shell structure of the measuring cell is made of an electrically non-conductive material;
- detect a radio-frequency electric field formed in the chamber by the output element of the radio-frequency signal;
- measure at least one property of the sample on the basis of at least one resonance frequency.

11. A method for measuring a sample in a measuring cell, the method comprising:
- coupling a radio-frequency signal, which has a wavelength greater than the largest interior measurement of a chamber, through a loop coupling of an input element inductively to the helix conductor in the chamber, which comprises a shell structure made of electrically conductive material, for the purpose of forming a helix resonance by means of the helix conductor of the measuring cell, both ends of the helix conductor having the same coupling to the shell structure of the chamber in such a manner that the helix conductor is at both ends short-circuited to the shell structure, while the shell structure of the measuring cell is made of an electrically non-conductive material;
- detecting a radio-frequency electric field formed in the chamber with the output element of the radio-frequency signal by forming with loop coupling an inductive coupling to the resonating helix conductor, and transmitting a radio-frequency signal for measuring.

* * * * *